US00PP13333P2

(12) United States Plant Patent
Kristiansen

(10) Patent No.: US PP13,333 P2
(45) Date of Patent: Dec. 10, 2002

(54) ASTER PLANT NAMED 'VICTORIA CELESTE'

(75) Inventor: Kell Kristiansen, Årslev (DK)

(73) Assignee: Aster Klubben, Aarslev (DK)

( * ) Notice: Subject to any disclaimer, the term of this patent is extended or adjusted under 35 U.S.C. 154(b) by 0 days.

(21) Appl. No.: 10/077,379

(22) Filed: Feb. 15, 2002

(51) Int. Cl.[7] ..... A01H 5/00

(52) U.S. Cl. ..... Plt./355

(58) Field of Search ..... Plt./355

*Primary Examiner*—Kent L. Bell
(74) *Attorney, Agent, or Firm*—C. A. Whealy

(57) ABSTRACT

A distinct cultivar of Aster plant named 'Victoria Celeste', characterized by its upright and outwardly spreading plant habit; dark green foliage; freely flowering habit; and decorative-type inflorescences with purple-colored ray florets.

1 Drawing Sheet

BOTANICAL CLASSIFICATION/CULTIVAR DESIGNATION

*Aster novi-belgii* cultivar 'Victoria Celeste'.

BACKGROUND OF THE INVENTION

The present Invention relates to a new and distinct cultivar of Aster plant, botanically known as *Aster novi-belgii* and hereinafter referred to by the name 'Victoria Celeste'.

The new Aster is a product of a planned breeding program conducted by the Inventor in Årslev, Denmark. The objective of the breeding program is to create new potted Aster cultivars with uniform plant growth habit, desirable floret colors, and good postproduction longevity.

The new Aster originated from a cross made by the Inventor in Årslev, Denmark, of a proprietary Aster selection identified as code number F3, not patented, as the female, or seed, parent with a proprietary Aster selection identified as code number 180/97, not patented, as the male, or pollen, parent. The new Aster was discovered and selected by the Inventor as a single flowering plant within the progeny of the stated cross grown in a controlled environment in Årslev, Denmark. The selection of this plant was based on its uniform plant growth habit and desirable inflorescence form and ray floret color.

Asexual reproduction of the new Aster by vegetative tip cuttings was first conducted in Årslev, Denmark during the Spring of 1999. Asexual reproduction by cuttings has shown that the unique features of this new Aster are stable and reproduced true to type in successive generations.

SUMMARY OF THE INVENTION

The cultivar 'Victoria Celeste' has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Victoria Celeste'. These characteristics in combination distinguish 'Victoria Celeste' as a new and distinct Aster:

1. Upright and outwardly spreading plant habit.
2. Dark green foliage.

3. Freely flowering habit.
4. Decorative-type inflorescences with purple-colored ray florets.

Plants of the new Aster are more compact than plants of the female parent selection. In addition, plants of the new Aster differ from plants of the female parent selection in ray floret coloration.

Plants of the new Aster have more ray florets per inflorescence than plants of the male parent selection. In addition, plants of the new Aster differ from plants of the male parent selection in ray floret coloration.

Plants of the new Aster can be compared to plants of the cultivar 'Kamma Vyking', not patented. In side-by-side comparisons conducted in Broby, Denmark, plants of the new Aster differed from plants of the cultivar 'Kamma Vyking' in the following characteristics:

1. Plants of the new Aster were more freely flowering than plants of the cultivar 'Kamma Vyking'.
2. Inflorescences of the new Aster had more ray florets than inflorescences of the cultivar 'Kamma Vyking'.

BRIEF DESCRIPTION OF THE PHOTOGRAPHS

The accompanying colored photographs illustrate the overall appearance of the new Aster showing the colors as true as it is reasonably possible to obtain in colored reproductions of this type. Colors in the photographs may differ from the color values cited in the detailed botanical description which accurately describe the colors of the new Aster.

The photograph at the top of the sheet comprises a side perspective view of a typical flowering plant of 'Victoria Celeste'.

The photograph at the bottom of the sheet comprises a close-up view of typical inflorescences and leaves of 'Victoria Celeste'.

DETAILED BOTANICAL DESCRIPTION

In the following description, color references are made to The Royal Horticultural Society Colour Chart, 1995 Edition, except where general terms of ordinary dictionary significance are used. The aforementioned photographs, following observations and measurements describe plants grown and flowered during the summer in Broby, Denmark, in a glass-covered greenhouse and under conditions which approximate those generally used in commercial potted Aster production. During the production of these plants, day and night temperatures averaged 21° C. One cutting was planted in 10-cm containers and pinched once. Plants were about 12 weeks old when the photographs and the botanical description were taken. Measurements and numerical values represent averages of typical flowering plants.

Botanical classification: *Aster novi-belgii* cultivar 'Victoria Celeste'.

Parentage:

*Female, or seed, parent.*—Proprietary *Aster novi-belgii* selection identified as code number F3, not patented.

*Male, or pollen, parent.*—Proprietary *Aster novi-belgii* selection identified as code number 180/97, not patented.

Propagation:

*Type.*—Terminal tip cuttings.

*Time to initiate roots.*—Summer: About 12 days at 21° C. Winter: About 13 days at 21° C.

*Root description.*—White, close to 155D; fine; fibrous.

*Rooting habit.*—Freely branching.

Plant description:

*Appearance.*—Herbaceous decorative-type potted Aster. Stems upright and outwardly spreading. Appropriate for 10 to 15-cm containers.

*Plant height.*—About 19.5 cm.

*Plant width.*—About 22.5 cm.

*Lateral branches* (*peduncles*).—Length: About 15.5 cm. Diameter: About 3 mm. Strength: Strong. Angle: About 45° from vertical. Texture: Slightly pubescent. Color: 137B.

*Foliage description.*—Arrangement: Alternate; sessile. Length: About 4 cm. Width: About 7.5 mm. Shape: Lanceolate. Apex: Acute. Base: Cuneate. Margin: Entire. Texture, upper and lower surfaces: Glabrous, smooth; leathery. Color: Young and mature foliage, upper surface: 147A; venation, close to 147A. Young and mature foliage, lower surface: 137C; venation, close to 137C.

Inflorescence description:

*Appearance.*—Decorative-type inflorescence form with narrowly obovate-shaped ray florets. Inflorescences terminal or axillary. Disc and ray florets arranged acropetally on a capitulum. Not fragrant. Inflorescences persistent.

*Flowering response.*—Under natural conditions, plants flower in the summer in Broby, Denmark.

*Postproduction longevity.*—Inflorescences maintain good color and substance for about three weeks on the plant in an interior environment.

*Quantity of inflorescences.*—About six to nine inflorescences develop per lateral branch.

*Inflorescence bud.*—Length: About 6.5 mm. Diameter: About 5.5 mm. Shape: Ovoid. Color: Close to 147A.

*Inflorescence size.*—Diameter: About 3.25 cm. Depth (height): About 1.25 cm. Diameter of disc: About 5 mm.

*Ray florets.*—Shape: Narrowly obovate. Orientation: Initially upright, then perpendicular to the peduncle. Aspect: Mostly flat; straight to slightly concave. Length: About 1.6 cm. Width: About 1.5 mm. Apex: Rounded. Base: Attenuate. Margin: Entire. Texture, upper and lower surfaces: Smooth, glabrous. Number of ray florets per inflorescence: About 225 arranged in more than six rows. Color: When opening, upper and lower surfaces: 81C. Fully expanded, upper surface: 81C; fading to 81D with subsequent development. Towards the base, close to 155D. Fully expanded, lower surface: 81D.

*Disc florets.*—Arrangement: Massed at center of receptacle. Shape: Tubular, elongated. Apex: Acute. Length: About 1.5 mm. Width: Less than 1 mm. Number of disc florets per inflorescence: About 10 to 20. Color: 137D to 150D with development.

*Phyllaries.*—Quantity per inflorescence: About 30 to 40. Length: About 2 mm. Width: Less than 1 mm. Shape: Narrowly obovate. Apex: Acuminate. Base: Truncate. Texture, upper and lower surfaces: Smooth. Color, upper and lower surfaces: 137A.

*Reproductive organs.*—Androecium: Present on disc florets only. Quantity per disc floret: One. Anther shape: Narrowly obovate. Anther length: About 1 mm. Anther color: 12A. Pollen amount: Moderate. Pollen color: 12A. Gynoecium: Present on both ray and disc florets. Pistil quantity per floret: One. Stigma shape: Bifurcate. Stigma color: 155A.

*Seed.*—Seed production has not been observed.

Disease/pest resistance: Resistance to pathogens and pests common to Asters has not been observed on plants grown under commercial greenhouse conditions.

It is claimed:

1. A new and distinct cultivar of Aster plant named 'Victoria Celeste', as illustrated and described.

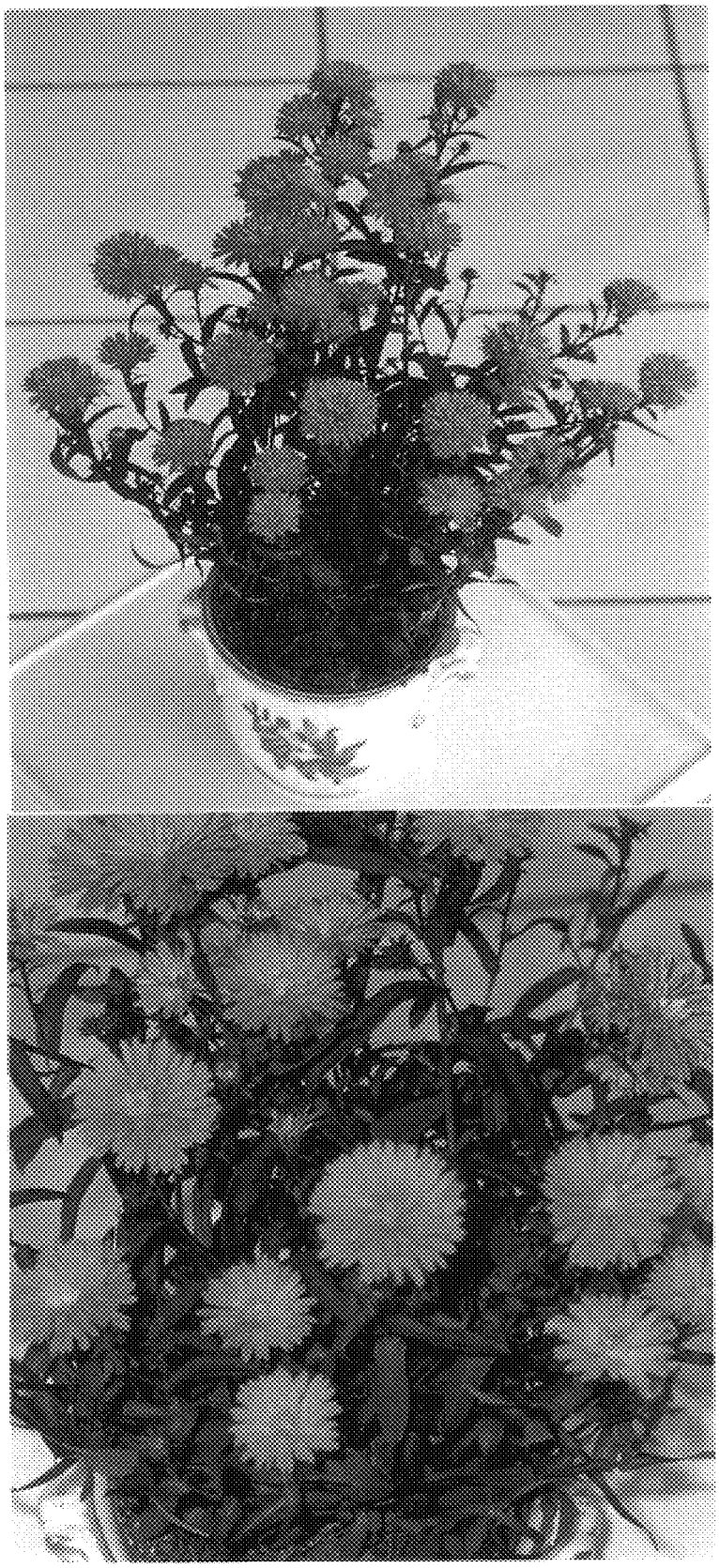

* * * * *